(12) United States Patent
Santogrossi et al.

(10) Patent No.: US 10,391,311 B2
(45) Date of Patent: Aug. 27, 2019

(54) COCHLEAR IMPLANTS

(71) Applicant: Advanced Bionics AG, Staefa (CH)

(72) Inventors: Thomas Santogrossi, Porter Ranch, CA (US); Jian Xie, Valencia, CA (US); Lin Li, Valencia, CA (US); Markus Heerlein, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 62 days.

(21) Appl. No.: 15/537,411

(22) PCT Filed: Jan. 21, 2015

(86) PCT No.: PCT/US2015/012317
§ 371 (c)(1),
(2) Date: Jun. 17, 2017

(87) PCT Pub. No.: WO2016/118127
PCT Pub. Date: Jul. 28, 2016

(65) Prior Publication Data
US 2018/0236234 A1  Aug. 23, 2018

(51) Int. Cl.
*A61N 1/36* (2006.01)
*A61N 1/375* (2006.01)
*A61N 1/05* (2006.01)

(52) U.S. Cl.
CPC ....... *A61N 1/36038* (2017.08); *A61N 1/0541* (2013.01); *A61N 1/36036* (2017.08); *A61N 1/375* (2013.01); *A61N 1/3754* (2013.01); *A61N 1/3758* (2013.01)

(58) Field of Classification Search
CPC .................................................. A61N 1/36038
See application file for complete search history.

(56) References Cited

U.S. PATENT DOCUMENTS

| 6,040,082 A | 3/2000 | Haas et al. |
|---|---|---|
| 6,607,843 B2 | 8/2003 | Ruth, II et al. |
| 7,341,802 B1 | 3/2008 | Ota et al. |
| 7,668,597 B2 | 2/2010 | Engmark et al. |

(Continued)

FOREIGN PATENT DOCUMENTS

| WO | WO 2006/081361 A2 | 8/2006 |
|---|---|---|
| WO | WO 2010/085838 A1 | 8/2010 |
| WO | WO 2011/143266 A2 | 11/2011 |

OTHER PUBLICATIONS

PCT International Search and Written Opinion dated Sep. 18, 2015 for PCT App. Ser. No. PCT/US2015/012317.

*Primary Examiner* — Carl H Layno
*Assistant Examiner* — Jennifer L Ghand
(74) *Attorney, Agent, or Firm* — Henricks Slavin LLP

(57) ABSTRACT

A cochlear implant including a cochlear lead, an antenna, a processor case, and a printed circuit board assembly located within the processor case. The processor case may include a base with a bottom wall and first and second side walls that together define a one-piece, unitary structure, a first end wall, attached to the bottom wall and to the first and second side walls, including a first plurality of feedthrough pins, a second end wall, attached to the bottom wall and to the first and second side walls, including a second plurality of feedthrough pins, and a cover attached to the first and second side walls and to the first and second end walls.

19 Claims, 4 Drawing Sheets

(56) References Cited

U.S. PATENT DOCUMENTS

| | | | |
|---|---|---|---|
| 2005/0159791 A1* | 7/2005 | Daly | H04R 25/606 607/57 |
| 2012/0016444 A1 | 1/2012 | Koester | |
| 2012/0221078 A1* | 8/2012 | Leigh | A61N 1/3754 607/57 |
| 2014/0254124 A1 | 9/2014 | Raje et al. | |
| 2016/0082249 A1* | 3/2016 | Thenuwara | A61N 1/375 607/57 |

* cited by examiner

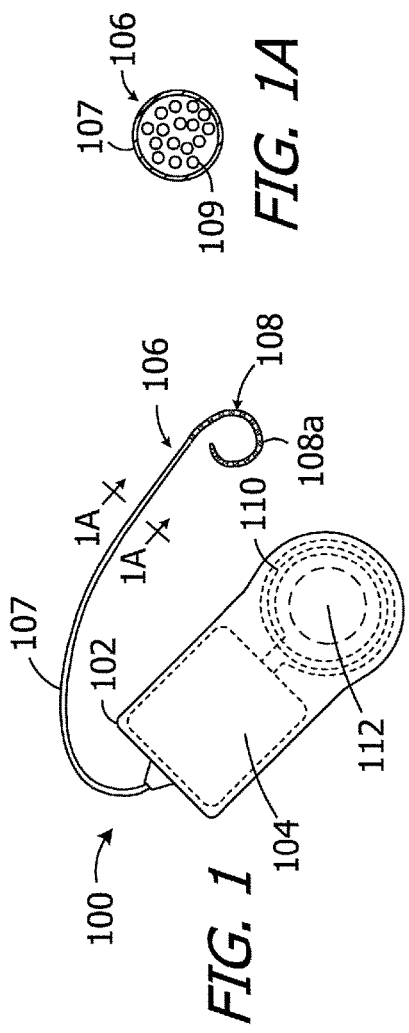
FIG. 1
FIG. 1A
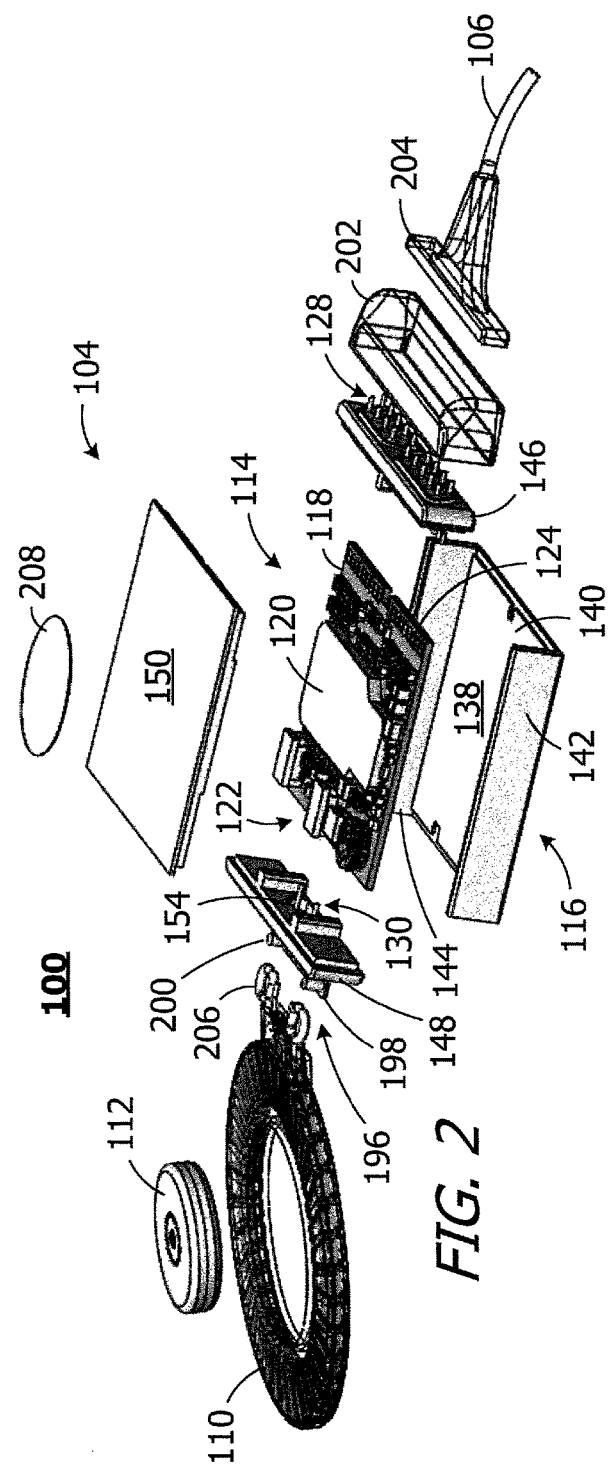
FIG. 2

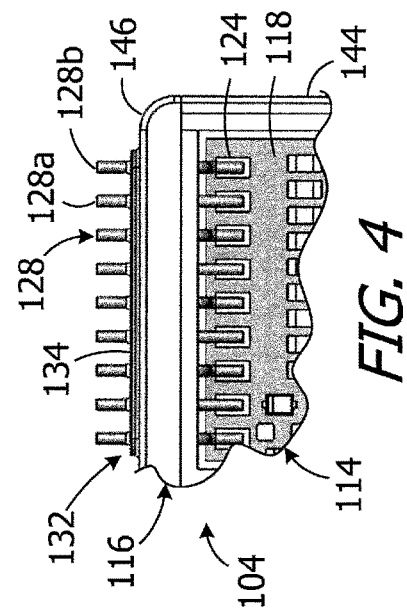
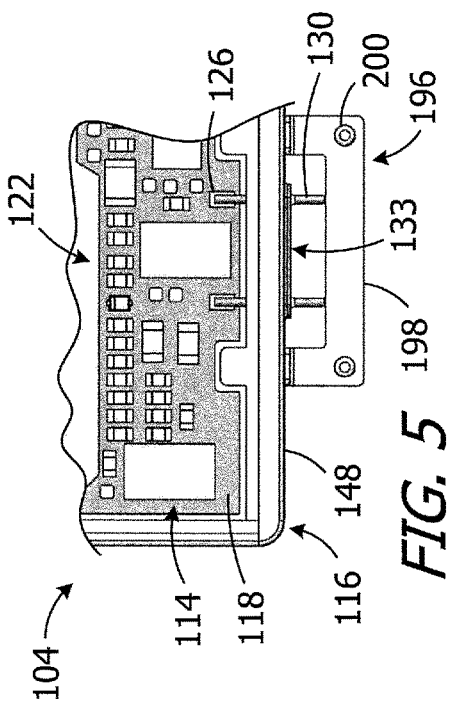
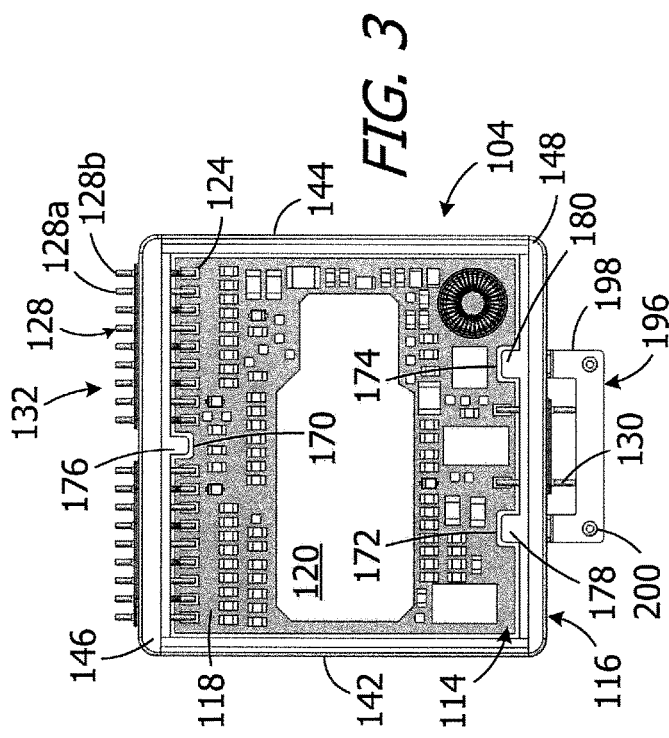
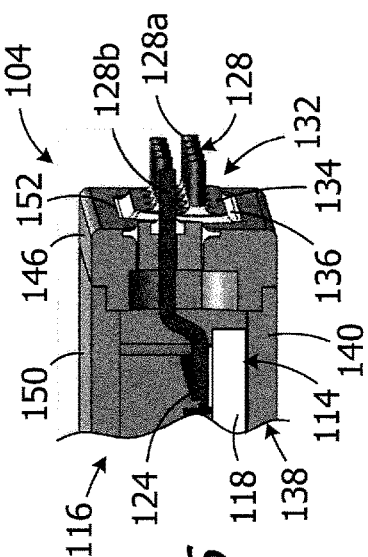

COCHLEAR IMPLANTS

CROSS-REFERENCE TO RELATED APPLICATIONS

This application is the U.S. National Stage of PCT App. Ser. No. PCT/US2015/012317, filed Jan. 21, 2015.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety.

As alluded to above, some ICS systems include an implant, a sound processor unit (e.g., a body worn processor or behind-the-ear processor), and a microphone that is part of, or is in communication with, the sound processor unit. The cochlear implant communicates with the sound processor unit and, to that end, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver.

The present inventors have determined that conventional cochlear implants, as well as the methods of assembling such implants, are susceptible to improvement. For example, the present inventors have determined that it would be desirable to reduce the thickness of cochlear implants, improve the reliability of cochlear implants, and reduce the manufacturing costs of cochlear implants.

SUMMARY

A cochlear implant may include a cochlear lead, an antenna, a processor case, and a printed circuit board assembly located within the processor case. The processor case may include a base with a bottom wall and first and second side walls that together define a one-piece, unitary structure, a first end wall, attached to the bottom wall and to the first and second side walls, including a first plurality of feedthrough pins, a second end wall, attached to the bottom wall and to the first and second side walls, including a second plurality of feedthrough pins, and a cover attached to the first and second side walls and to the first and second end walls.

A method of assembling a cochlear implant may include securing a printed circuit board assembly to a processor case base, the processor case base having a bottom wall and first and second side walls that together define a one-piece, unitary structure, attaching a first end wall to the bottom wall and to the first and second side walls, the first end wall including a first plurality of feedthrough pins, attaching a second end wall to the bottom wall and to the first and second end walls, the second end wall including a second plurality of feedthrough pins, connecting the feedthrough pins to electrical contacts on the printed circuit board assembly, attaching a cover to the first and second side walls and to the first and second end walls to complete a processor case, connecting a cochlear lead to the first plurality of feedthrough pins, and connecting an antenna to the second plurality of feedthrough pins.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a plan view of a cochlear implant in accordance with one embodiment of a present invention.

FIG. 1A is a section view taken along line 1A-1A in FIG. 1.

FIG. 2 is an exploded view of the cochlear implant illustrated in FIG. 1.

FIG. 3 is a plan view of the exemplary processor assembly illustrated in FIGS. 1 and 2 with the cover removed.

FIG. 4 is a plan view of a portion of the exemplary processor assembly illustrated in FIGS. 1 and 2 with the cover removed.

FIG. 5 is a plan view of a portion of the exemplary processor assembly illustrated in FIGS. 1 and 2 with the cover removed.

FIG. 6 is a section view of a portion of the processor assembly illustrated in FIGS. 1 and 2.

DETAILED DESCRIPTION OF THE EXEMPLARY EMBODIMENTS

Figure 8:
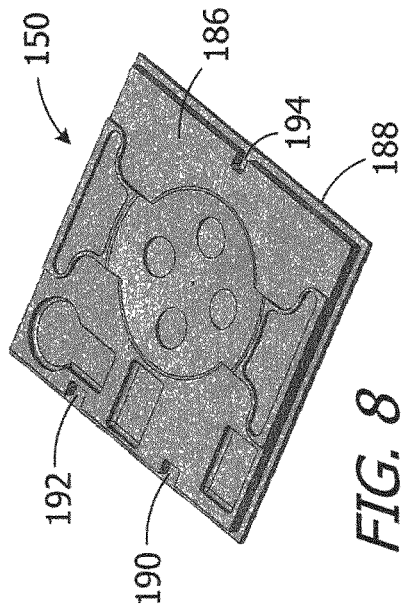
FIG. 8 is a perspective view of a portion of the exemplary processor assembly illustrated in FIGS. 1 and 2.

The following is a detailed description of the best presently known modes of carrying out the inventions. This description is not to be taken in a limiting sense, but is made merely for the purpose of illustrating the general principles of the inventions.

The exemplary cochlear stimulator 100 illustrated in FIGS. 1, 1A and 2 includes a flexible housing 102 formed from a silicone elastomer or other suitable material, a processor assembly 104, a cochlear lead 106, and an antenna 110 that may be used to receive data and power by way of an external antenna that is associated with, for example, a sound processor unit. The cochlear lead 106 may include a flexible body 107, an electrode array 108 at one end of the flexible body, and a plurality of wires 109 that extend from the electrodes 108a (e.g., platinum electrodes) in the array 108 to the other end of the flexible body. A positioning element (i.e., a magnet or other ferromagnetic material) 112 may be proved to insure that an external antenna (not shown) is properly positioned relative to the antenna 110. The exemplary processor assembly 104, which is connected to the electrode array 108 and antenna 110 in the manner described below, includes a printed circuit board assembly ("PCBA") 114 that is located within a hermetically sealed case 116. The exemplary antenna 110 includes transmission wires (e.g., gold or other suitable metal wires) and parallel polymer support wires (e.g., ultra high molecular weight polyethylene wires) arranged in loops to form a coil. Shield wire (sometimes referred to as a "spiral shield") may be wrapped around the antenna coil to confine the electrical field of the antenna coil.

The PCBA 114 includes a printed circuit board ("PCB") 118 on which the electronic components, such as a stimulation processor 120 and receiver circuitry 122, and electrical contacts 124 and 126 (e.g., gold plated pads) are surface mounted. The exemplary PCB 118 may be a planar (or "flat") PCB and may be formed from an FR4 grade glass-reinforced epoxy laminate. All of the electrical components and contacts are located on the same plane. In the illustrated embodiment, and referring to FIGS. 3-6, there are eighteen (18) electrical contacts 124 for connection the electrodes array 108 on the cochlear lead 106 and there are two (2) electrical contacts 126 for connection to the transmission wires of the antenna 110. As such, there are eighteen (18) feedthrough pins 128 that extend into the case 116 on the electrical lead side and two (2) feedthrough pins 130 on the antenna side. The feedthrough pins 128 are separated into the two groups of nine (9) feedthrough pins. There are also two different pin configurations within each group of feedthrough pins 128, i.e., linear feedthrough pins 128a that are linear from one end to the other and non-linear feedthrough pins 128b that are not linear from one end to the other. The exemplary non-linear feedthrough pins 128b have first and second parallel portions that are connected by an intermediate portion that extends in a direction that is transverse to the parallel portions (FIG. 6). The feedthrough pins 128 are arranged such that, on the exterior of the case 116, the ends of the pins define two rows of feedthrough pins within each group. The ends of the linear feedthrough pins 128a form a bottom row and the ends of the non-linear feedthrough pins 128b form a top row in the illustrated orientation. The ends of the feedthrough pins 128 within the interior of the case 116, however, form a single row due to the non-linear configuration of the feedthrough pins 128b. The end of each feedthrough pin 128 is vertically and horizontally aligned with a respective one of the associated electrical contacts 124.

As a result of the above-described feedthrough pin configuration, the ends of the feedthrough pins 128 may be efficiently and cost effectively soldered to the electrical contacts 124. For example, the ends of the feedthrough pins 128 may be simultaneously soldered to the electrical contacts 124 using hot bar soldering and, in some instances, the ends of the feedthrough pins may be pre-tined. Similarly, the two feedthrough pins 130 are linear and the end of the pins within the case 116 are vertically and horizontally aligned with a respective one of the associated electrical contacts 126 and may be readily soldered. In other instances (not shown), tabs formed from a nickel-cobalt ferrous alloy sold under the tradename Kovar™ may be bonded to the PCB 118 by soldering, brazing or epoxy adhering to form the electrical contacts and laser welding may be employed to bond the ends of the feedthrough pins to the contacts.

Referring more specifically to FIGS. 3 and 6, each group of nine (9) feedthrough pins 128 in the illustrated embodiment is part of a feedthrough assembly 132 that also includes a ceramic base 134 and a titanium flange 136. A similar feedthrough assembly 133 (FIG. 5) is employed on antenna side of the case 116.

Referring to FIGS. 2-6, the exemplary case 116 includes a base 138 with, in the illustrated orientation, a bottom wall 140 and first and second side walls 142 and 144 that are opposite one another and perpendicular to the bottom wall. The base 138 in the illustrated implementation is a one-piece, unitary structure with side walls 142 and 144 that are parallel to one another and perpendicular to the bottom wall 140. As used herein, a "one-piece, unitary structure" is a structure that is formed from a single piece of material, as opposed to multiple pieces that are separately manufactured and then secured to one another through the use of welds, adhesives, mechanical fasteners and/or interlocks, or other instrumentalities. The base 138 may, for example, be formed by machining or stamping a single work piece or blank. The case 116 also includes end walls 146 and 148, which are attached to the bottom and side walls 140-144 of the base 138 during the assembly process, as well as a cover 150, which is attached to the side and end walls during the assembly process, as is discussed in greater detail below with reference to FIG. 8. The end wall 146 includes a pair of apertures 152 (FIG. 6) in which the feedthrough assemblies 132 are mounted, while the end wall 148 includes an aperture 154 (FIG. 2) for the feedthrough assembly 133. The feedthrough assemblies 132 and 133 are respectively secured to the end walls 146 and 148 by laser welding or other suitable technique.

Figure 7:
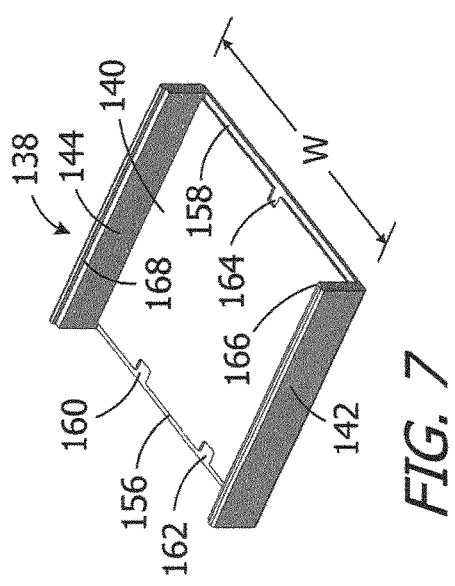
FIG. 7 is a perspective view of a portion of the exemplary processor assembly illustrated in FIGS. 1 and 2.

The exemplary case 116 also includes various features that facilitate assembly and alignment. To that end, and as illustrated in FIG. 7, the bottom wall 140 of the exemplary base 138 includes grooves 156 and 158 and plurality of slots 160-164, while the side walls 142 and 144 respectively include grooves 166 and 168. Turning to FIG. 3, the PCB 118 also includes a plurality of slots 170-174, while the end wall 146 includes a projection 176 and the end wall 148 includes projections 178 and 180. The end walls 144 and 146 also include respective grooves 182 and 184 that extend around the perimeter of their inner surfaces. The cover 150 (FIG. 8) includes a main body 186 and a flange 188 that projects outwardly around the perimeter of the main body. The cover 150 also includes a plurality of slots 190-194. The inner surface of the exemplary cover 150 includes various indentations (not numbered) that accommodate taller components on the PCBA 114.

A mounting bracket 196, with a flange 198 and a pair of posts 200, may be provided on the case end wall 148 for the antenna 110, as shown in FIGS. 3 and 5. The mounting bracket 196 includes an aperture that is configured to provide sufficient clearance for the welding electrodes that weld the transmission wires of the antenna 110 to the feedthrough pins 130 in the manner described below. The support wires of the antenna 110 are formed into loops 206 that are mounted onto the posts 200.

Figure 9:
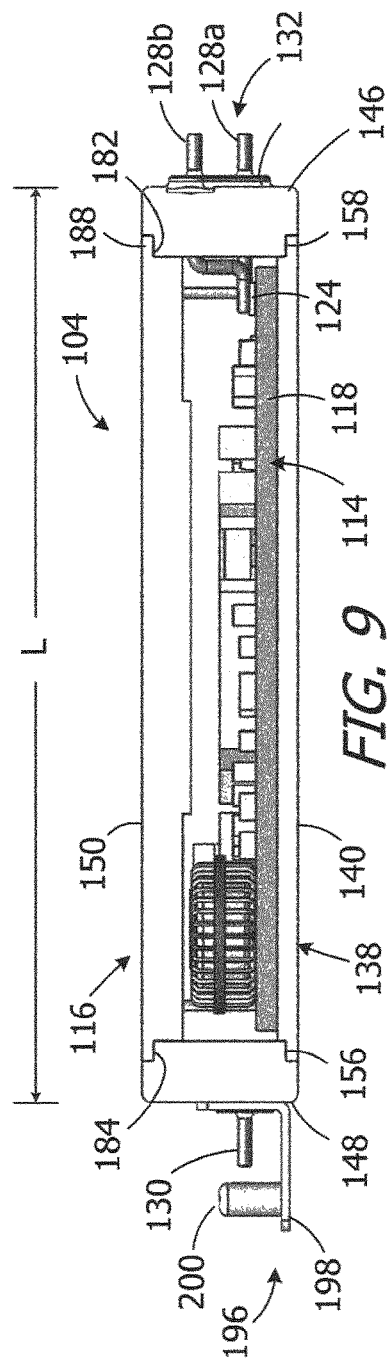
FIG. 9 is section view of the processor assembly illustrated in FIGS. 1 and 2.
Figure 9A:
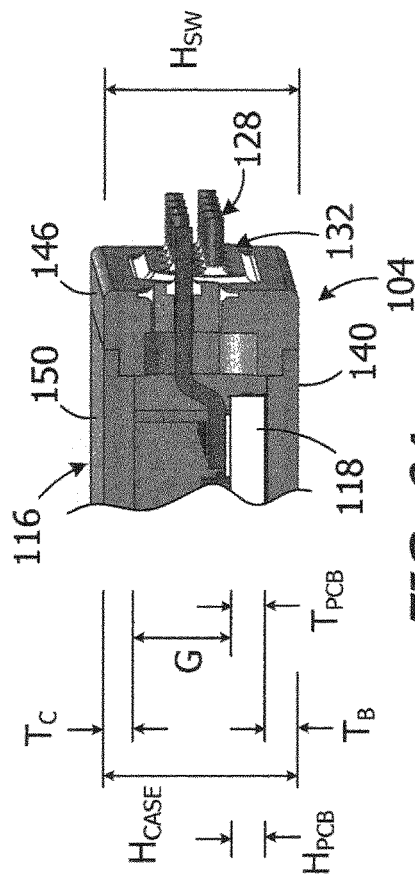
FIG. 9A is a section view of a portion of the processor assembly illustrated in FIGS. 1 and 2.

With respect to the materials and dimensions of the processor assembly 104, and although the present inventions are not limited to such materials and dimensions unless claimed, the exemplary components of the processor assembly case 116 (i.e., the base 138, end walls 146 and 148, and cover 150) may be formed from material such as commercial pure titanium or titanium alloys. Referring to FIGS. 7 and 9, the length L of the exemplary case 116, from the outer surface of the end wall 146 to the outer surface of the end wall 148, may range from 18 mm to 22 mm and is 20 mm in the illustrated embodiment, while the width W of the case 116, from the outer surface of the side wall 142 to the outer surface of the side wall 144 may range from 21 mm to 25 mm and is 23 mm in the illustrated embodiment. Turning to FIG. 9A, the height $H_{CASE}$ of the case 116 may range from 3.6 mm to 4.0 mm and is 3.8 mm in the illustrated embodiment. The thicknesses $T_B$ of the base bottom wall 140 and side walls 142 and 144 may range from 0.5 mm to 0.7 mm and is 0.6 mm in the illustrated embodiment. The height $H_{SW}$ of the side walls 142 and 144 (including the thickness of the bottom wall 140) is the same as the height of the end walls 146 and 148 may range from 3.6 mm to 4.0 mm and is 3.8 mm in the illustrated embodiment. It should also be noted that the height $H_{CASE}$ of the case 116, which is less than length L and width W, is equal to the height $H_{SW}$ of the side walls 142 and 144 because the cover flange 188 fits into the side and end wall grooves as described below with reference to FIG. 10. The average thicknesses $T_C$ of the cover 150, whose thickness varies and whose thickness is larger where the cover abuts the inner surfaces of the side walls 142 and 144, may range from 0.6 mm to 0.8 mm and is 0.7 mm in the illustrated embodiment. The thicknesses $T_{PCB}$ of the PCB 118 may range from 0.4 mm to 0.7 mm and is 0.6 mm in the illustrated embodiment. It should be noted here that, because the PCB 118 is flat, e.g., does not have any portions that are bent away from the base bottom wall 140, the maximum distance from the inner surface of the bottom wall 140 to the top surface of the PCB 118, i.e., the PCB height $H_{PCB}$, is thickness of the PCB and may range from 0.4 mm to 0.7 mm and is 0.6 mm in the illustrated embodiment. So configured, there is a gap between the top surface of the PCB 118 and the inner surface of the cover 150 that may range from 1.8 mm to 2.1 mm and is 2.0 mm in the illustrated embodiment.

So configured, the present case 116 defines various ratios and relationships that maximize its effectiveness. For example, for a case 116 whose height $H_{CASE}$ is less than or equal to 4.0 mm, the ratio of the case height $H_{CASE}$ to the PCB height $H_{PCB}$ may range from 5 to 10 in some embodiments, may range from 6 to 9 in some embodiments, may range from 6 to 7 in some embodiments, and is 6.4 in the illustrated implementation. Such ratios result in a more compact case than those associated with conventional cochlear implants. It should also be noted that such ratios are applicable to cases and/or PCBs with heights that are less than those described in the preceding paragraph.

A process of manufacturing the processor assembly 104 from the various components described above may proceed as follows. First, the PCBA 114 is secured to the bottom wall 140 of the base 138 between the side walls 142 and 144 with an adhesive, such as silicone adhesive, epoxy adhesive or double sided adhesive tape, or through the use of another suitable instrumentality. The PCB slots 170-174 will be aligned with the bottom wall slots 160-164. Next, the end wall 146, which includes the feedthrough assemblies 132, may be positioned on the base 138 such that the groove 182 is aligned with the bottom wall groove 158 and the projection 176 is located within bottom wall slot 164 and PCB slot 170. So arranged, the ends of the feedthrough pins 128 will be aligned with the electrical contacts 124 of the PCBA 114. The end wall 146 may then be secured to the base 138 through the use of laser welding or another suitable technique. Similarly, the end wall 148, which includes the feedthrough assembly 133, may be positioned on the base 138 such that the groove 184 is aligned with the bottom wall groove 156 and the projections 178 and 180 are located within bottom wall slots 160 and 162 as well as PCB slots 172 and 174. So arranged, the ends of the feedthrough pins 130 will be aligned with the electrical contacts 126 of the PCBA 114. The ends of the feedthrough pins 128 and 130 may then be soldered or otherwise bonded to the electrical contacts 124 and 126. Finally, the cover 150 may be positioned on the base 138 and end walls 146 and 148 such that the flange 188 is located within the base side walls grooves 166 and 168 and the end wall grooves 182 and 184. The cover 150 may then be secured to the base 138 and sidewalls 144 and 146 through the use of laser welding or another suitable technique. The result of this process is the hermetically sealed case 116 with the PCBA 114 within the case and the feedthrough pins 128 and 130 extending from the inside of the case to the outside of the case.

The cochlear implant, including the completed processor assembly 104, may then be assembled. The wires 109 (FIG. 1A) from the cochlear lead 106 may be connected to the ends of the respective feedthrough pins 128 using any suitable technique. For example, the spacing between the feedthrough pins 128 in the feedthrough assemblies 132 is sufficient to permit the use of opposed gap resistance welding, which is a two sided process where the side surface of a pin, a strip of platinum and a wire is sandwiched between a pair of welding electrodes as current passes from one electrode to the other. The resistance of the pin, platinum, wire and electrodes produces heat, thereby melting the platinum and bonding the wire to the pin. Another suitable welding technique involves bonding each wire to an electrical connector formed from a thin strip of conductive material at the end of each pin. An epoxy header 202 may be adhered to the end wall 146 to protect the connection between the processor assembly 104 and a cochlear lead 106, including the connection between the lead wires 109 and the feedthrough pins 128. A header 204, formed from liquid silicone rubber or epoxy, may be used to maintain the lead wires 109 in their intended positions.

Turning to the antenna 110, and as noted above, the transmission wires of the antenna may be connected to the ends of the feedthrough pins 130 using gap resistance welding where the top and bottom welding electrodes that obtain access to the feedthrough pins by way of the aperture in the bracket 196. The shield wires of the antenna 110 may be welded to the bracket 196 and support wire loops 206 may be mounted onto the posts 200. Once the processor assembly 104, cochlear lead 106 and antenna 110 are connected to one another, the flexible housing 102 (FIG. 1) may be formed by way of, for example, an insert molding process with the magnet 112 in its final location.

In some implementations, a platinum disk 208 (FIG. 2) may be mounted to the exterior of the case 116, which is noted above may be formed from titanium. The platinum disk 208, which may be resistance spot welded to the cover 150 prior to assembly of the case 116, serves as the case ground and provides a better return path for the stimulation energy applied by the electrodes 108*a* in the array 108 than the titanium case 116. Platinum is employed here because it has the same potential as the exemplary platinum electrodes 108*a* on lead. Also, because platinum is a noble metal, oxides will not form on the disk 208 over time.

Figure 10:
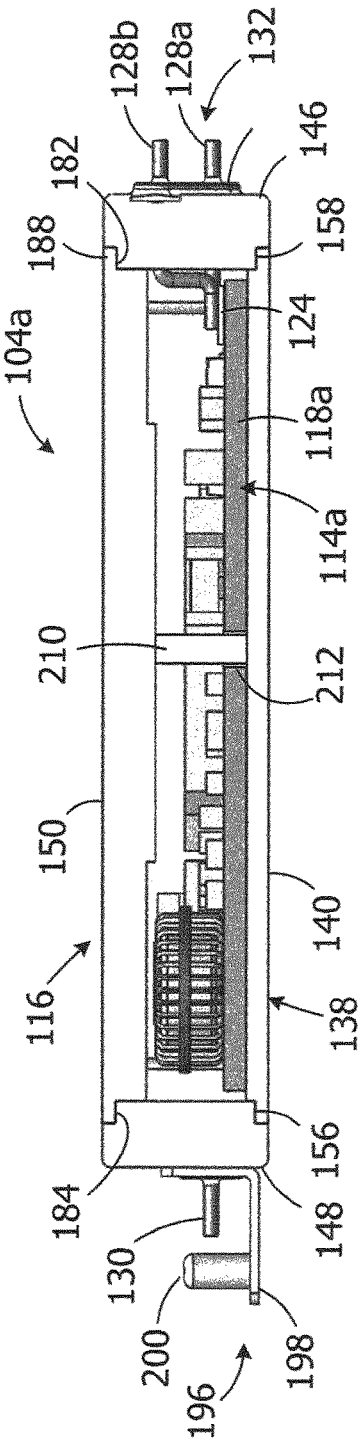
FIG. 10 is a section view of another exemplary processor assembly.

In some implementations, the processor assembly case may be provided with additional structural support. To that end, the processor assembly 104*a* illustrated in FIG. 10 is substantially similar to processor assembly 104 and similar elements are represented by similar reference numerals. Here, however, a post 210 (e.g., a titanium post) is positioned between and is in contact with the bottom wall 140 and the cover 150. The PCB assembly 114*a* has a PCB 118*a* with an aperture 212 to permit passage of the post 210.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant, comprising:
a cochlear lead including a flexible body, a plurality of electrodes on the flexible body, and a plurality of wires within the flexibly body respectively connected to the plurality of electrodes;
an antenna;
a processor case including
  a multi-piece structure that includes
    a base with a bottom wall and first and second side walls that together define a one-piece, unitary structure,
    a first end wall, attached to the bottom wall and to the first and second side walls, including a first plurality of feedthrough pins having first ends respectively connected to the plurality of lead wires and second ends,
    a second end wall, attached to the bottom wall and to the first and second side walls, including a second plurality of feedthrough pins having first ends connected to the antenna and second ends,
    the base and the first and second end walls including respective features that facilitate alignment of the base with the first and second end walls, and
  a cover attached to the first and second side walls and to the first and second end walls; and
a printed circuit board assembly located within the processor case and including a printed circuit board, a processor on the printed circuit board, a first plurality of electrical contacts respectively connected to the second ends of the first plurality of feedthrough pins and second plurality of electrical contacts respectively connected to the second ends of the second plurality of feedthrough pins.

2. A cochlear implant as claimed in claim 1, wherein the printed circuit board is flat, the first plurality of electrical contacts are located in single plane and the second ends of the first plurality of feedthrough pins are connected to the first plurality of electrical contacts in the single plane.

3. A cochlear implant as claimed in claim 2, wherein the first plurality of feedthrough pins includes linear feedthrough pins that are linear from the first end to the second end and non-linear feedthrough pins that are not linear from the first end to the second end.

4. A cochlear implant as claimed in claim 3, wherein the non-linear feedthrough pins each include first and second parallel portions that are connected by an intermediate portion that extends in a direction that is transverse to the parallel portions.

5. A cochlear implant as claimed in claim 3, wherein the first ends of the linear feedthrough pins define a first row and the first ends of the non-linear feedthrough pins define a second row.

6. A cochlear implant as claimed in claim 1, wherein the first and second side walls are parallel to one another and perpendicular to the bottom wall.

7. A cochlear implant as claimed in claim 1, wherein the case defines a length and a width, and further defines a height that is less than the length, less than the width, and less than 4.0 mm;
the printed circuit board defines a height; and
the ratio of the case height to the printed circuit board height is from 5 to 10.

8. A cochlear implant as claimed in claim 7, wherein the ratio of the case height to the printed circuit board height is from 6 to 9.

9. A cochlear implant as claimed in claim 7, wherein the ratio of the case height to the printed circuit board height is from 6 to 7.

10. A cochlear implant as claimed in claim 1, wherein the base includes first and second grooves configured to receive respective portion of the first and second end walls.

11. A cochlear implant as claimed in claim 1, wherein the first and second end walls include respective grooves configured to receive respective portions of the base.

12. A method of assembling a cochlear implant, the method comprising the steps of:
securing a printed circuit board assembly to a processor case base, the processor case base having a bottom wall and first and second side walls that together define a one-piece, unitary structure, the printed circuit board assembly including a printed circuit board, a processor on the printed circuit board, a first plurality of electrical contacts, and second plurality of electrical contacts;
attaching a first end wall to the bottom wall and to the first and second side walls, the first end wall including a first plurality of feedthrough pins having first and second ends;
attaching a second end wall to the bottom wall and to the first and second end walls, the second end wall including a second plurality of feedthrough pins having first and second ends;
connecting the second ends of the first plurality of feedthrough pins to the first plurality of electrical contacts;
connecting the second ends of the second plurality of feedthrough pins to the second plurality of electrical contacts;
attaching a cover to the first and second side walls and to the first and second end walls to complete a processor case;
connecting a cochlear lead to the first ends of the first plurality of feedthrough pins; and
connecting an antenna to the first ends of the second plurality of feedthrough pins.

13. A method as claimed in claim 12, wherein
the printed circuit board is flat and the first plurality of electrical contacts are located in single plane; and
connecting the second ends of the first plurality of feedthrough pins comprises connecting the second ends of the first plurality of feedthrough pins to the first plurality of electrical contacts in the single plane.

14. A method as claimed in claim 13, wherein
the first plurality of feedthrough pins includes linear feedthrough pins that are linear from the first end to the second end and non-linear feedthrough pins that are not linear from the first end to the second end.

15. A method as claimed in claim 13, wherein
connecting the second ends of the first plurality of feedthrough pins comprises simultaneously soldering the second ends of the first plurality of feedthrough pins to the first plurality of electrical contacts in the single plane.

16. A method as claimed in claim 12, wherein
the printed circuit board is flat and the first plurality of electrical contacts are located in single plane; and
securing a printed circuit board assembly to a processor case base comprises securing the flat printed circuit board to the bottom wall.

17. A method as claimed in claim 12, wherein
the first and second side walls of the processor case base are parallel to one another and perpendicular to the bottom wall.

18. A method as claimed in claim 12, wherein
attaching a first end wall comprises welding a first end wall to the bottom wall and to the first and second side walls;
attaching a second end comprises welding a first end wall to the bottom wall and to the first and second side walls; and
attaching a cover comprises welding a cover to the first and second side walls and to the first and second end walls to complete a processor case.

19. A method as claimed in claim 12, further comprising the step of
molding a flexible housing over the processor case and antenna.

\* \* \* \* \*